(12) United States Patent
Warnock

(10) Patent No.: US 6,566,402 B2
(45) Date of Patent: May 20, 2003

(54) USE OF CITRATE-CONTAINING DIALYSATE FOR RENAL DIALYSIS TREATMENT

(75) Inventor: David G. Warnock, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/863,657

(22) Filed: May 23, 2001

(65) Prior Publication Data

US 2002/0004530 A1 Jan. 10, 2002

Related U.S. Application Data

(60) Provisional application No. 60/206,763, filed on May 24, 2000.

(51) Int. Cl.$^7$ .............................................. A61K 31/19
(52) U.S. Cl. ...................................................... 514/574
(58) Field of Search ......................................... 514/574

(56) References Cited

PUBLICATIONS

Medline AN 92174433, van der Meulen, J. et al, Clinical Nephrology, Jan., 1992 37 (1), 36–41, abstract.*

* cited by examiner

*Primary Examiner*—Rebecca Cook
(74) *Attorney, Agent, or Firm*—Benjamin Aaron Adler

(57) ABSTRACT

The present invention describes trisodium citrate-containing dialysates and production thereof. Also described are the applications of such dialysates as regional anticoagulants during hemodialysis and all modes of continuous renal replacement therapy which utilize any form of dialysis.

6 Claims, 1 Drawing Sheet

USE OF CITRATE-CONTAINING DIALYSATE FOR RENAL DIALYSIS TREATMENT

CROSS-REFERENCE TO RELATED APPLICATION

This non-provisional patent application claims benefit of provisional U.S. Ser. No. 60/206,763, filed May 24, 2000, now abandoned.

BACKGROUND OF THE INVENTION

1. Field of the Invention

The present invention relates generally to the field of medical therapy of renal disease. More specifically, the present invention relates to the use of trisodium citrate-containing dialysate solutions during hemodialysis and continuous renal replacement therapy, wherein trisodium citrate functions as a regional anticoagulant.

2. Description of the Related Art

Continuous arteriovenous hemodialysis (CAVHD) and other forms of continuous renal replacement therapy (CRRT) are being used increasingly as the major form of renal replacement therapy for critically ill patients with acute renal failure (ARF). Generally, the procedure has required systemic anticoagulation utilizing heparin or, in a few cases, prostacyclin to maintain filter patency. Although heparin is removed by continuous arteriovenous hemodialysis membranes, systemic anticoagulation is usually unavoidable with heparin and has been associated with an increased incidence of bleeding. In order to circumvent this problem, regional heparin anticoagulation has been tried, but this has not gained widespread acceptance due to the difficulty in accurately adjusting protamine doses. Similarly, continuous arteriovenous hemodialysis has been attempted with frequent saline flushes through the filter, but it has been difficult to keep the filter patent for longer than 24 hours.

U.S. Pat. No. 5,032,615 describes a technique employing sodium citrate as a regional anticoagulant for continuous arteriovenous hemodialysis (citrate CAVHD) which results in removal of excess water, electrolytes and catabolic toxins without requiring systemic anticoagulation. Citrate is infused at the origin of the extracorporeal circuit, and the citrate-calcium chelate is removed by diffusion across the membrane. The metabolic consequences of the sodium citrate load are compensated for by the use of a special dialysate containing no alkali, subnormal sodium concentration, and no calcium. Calcium homeostasis is restored by a peripheral infusion of calcium chloride into the patient.

Trisodium citrate (TSC) chelates calcium and thereby acts as a regional anticoagulant of extra-corporal circuits. Available from two different commercial vendors (as 4% and 46.7% solutions in sterile water), trisodium citrate is indicated and FDA approved as an anticoagulant for extra-corporal blood fractionation and cytopharesis. Direct intravenous infusion of this product is contraindicated, and in the case of 46.7% TSC can be exceedingly dangerous.

However, recent experience in critical care units has demonstrated that intravenously administered trisodium citrate is effective as an extra-corporal anticoagulant during various forms of acute dialysis, including continuous modes of hemofiltration and dialysis (1-5). With careful management of the ionized calcium and the rate of citrate infusion, it is possible to provide effective regional anticoagulation of the extra-corporal circuit without any adverse effects on the systemic clotting parameters (as assessed by Prothrombin Times (PT) and Partial Thromboplastin Times (PTT)).

The toxicities of this approach include metabolic alkalosis due to citrate accumulation and its subsequent metabolism to bicarbonate, and the effects of reduced systemic ionized calcium. Subjectively the patient may experience palpitations, perioral tingling and stomach cramps. Objective features of citrate toxicity include myocardial depression, arrhythmias and systemic alkalosis which may or may not include an anion gap. Proper surveillance of the rate of citrate administration and monitoring and correction of systemic ionized calcium may obviate these effects. Patients with severe liver disease may be prone to developing citrate toxicity and caution must be exercised in treating these patients with citrate (6). The recent clinical experience at the University of Alabama at Birmingham has demonstrated that 2% TSC infused in the prefilter circuit at 17.5 to 24.5 mmol citrate/hour, with dialysis against a normal saline dialysate solution (also containing 3 mM KCl, and 1 mM $MgSO_4$) provides safe and effective regional anticoagulation for continuous renal replacement therapy. The 2% TSC solution is isotonic and avoids problems with hypernatremia as has been observed with 4% TSC solutions. Furthermore, an isotonic saline dialysis solution (free of any buffer) is used at 1000 ml/hour which simplifies the preparation of the required solutions and minimizes administration errors. Infusion of 2% TSC in the prefilter circuit at 250 to 350 ml/hour (17.5 to 24.5 mmoles citrate/hour) provides adequate buffer input to maintain systemic acid-base balance, and results in effective calcium chelation of the extracorporal circuit with post-filter ionized calcium levels generally between 0.4 and 0.5 mM. Systemic ionized calcium is corrected to 1.0 to 1.1 mM by central infusion of calcium gluconate. This simplified approach to citrate regional anticoagulation has proven to be safe and effective and is now the standard of care for continuous renal replacement therapy in the intensive care units at the University of Alabama at Birmingham (7).

Heparin is the traditional anticoagulant used during hemodialysis procedures, but its use is accompanied with a number of serious side effects, including systemic anticoagulation, thrombocytopenia and suppressed aldosterone secretion. The effects on systemic coagulation make heparin administration very problematic in patients with gastrointestinal bleeding or traumatic injury in which hemostasis is impaired due to coagulation factor consumption or occult bleeding from wounds or vascular puncture sites. Furthermore, a number of patients are hyper-coagulable and even with maximal heparin administration, there is still clotting and loss of the extra-corporal dialysis circuit.

"No heparin" dialysis is possible but this requires frequent saline flushes of the extra-corporal circuit which is generally ineffective in the artificial kidney which is composed of a myriad of parallel minute fibers. Clotting of the circuit requires replacement of the entire circuit with attendant expense, inconvenience and loss of clinical efficacy. Recently, Ahmad et al. (8) described citric acid in dialysis solutions. Citric acid was used to prepare a "dry dialysate" for chronic dialysis. When reconstituted with water, the citric acid titrates bicarbonate to set the pH. Ionized Calcium was not monitored and chelation of Calcium resulted in anticoagulation was not considered.

While the use of trisodium citrate is approved for addition to whole blood in an extra-corporal circuit, the indication is for fraction of blood products and for cytopharesis. As such, the intravenous administration of trisodium citrate as a regional anticoagulant for hemo-dialysis represents an "off-label" use of this FDA-approved agent.

The prior art is deficient in a protocol presenting a mechanism whereby trisodium citrate can be used as a regional anticoagulant during hemodialysis and continuous renal replacement therapy by including it in the dialysate fluid, and thereby avoiding direct intravenous administration. The present invention fulfills this long-standing need and desire in the art.

SUMMARY OF THE INVENTION

The present invention is directed to a new dialysate solution which contains trisodium citrate, wherein trisodium citrate functions as a regional anticoagulant for dialysis treatment. This dialysate would not be administered intravenously. Diffusive flux of citrate across the dialysis membranes would provide base equivalents to the patient and would also chelate calcium in the extracorpal circuit. The major advantages of this approach is that it would be compatible with the current continuous renal replacement therapy (CRRT) devices in clinical use and could be readily adapted to acute intermittent hemodialysis.

In one embodiment of the present invention, there is provided a dialysate containing trisodium citrate.

In another embodiment of the present invention, there is provided a method of treating an individual having a renal disease by applying acute hemodialysis to the individual using the dialysate disclosed herein, wherein the dialysate is administered via dialysis circuits.

In still another embodiment of the present invention, there is provided a method of treating an individual having a renal disease by applying continuous renal replacement therapy to the individual using the dialysate disclosed herein, wherein the dialysate is administered via dialysis circuits.

In yet another embodiment of the present invention, there is provided a method of providing regional anticoagulation during acute hemodialysis in an individual in need of such treatment by administering the dialysate disclosed herein to the individual via dialysis circuits.

In still yet another embodiment of the present invention, there is provided a method of providing regional anticoagulation during continuous renal replacement therapy in an individual in need of such treatment by administering the dialysate disclosed herein to the individual via dialysis circuits.

Additional applications of the dialysate disclosed herein include correction of severe systemic metabolic alkalosis by greatly reducing the citrate delivery rate in the dialysis solution, and correction of severe systemic metabolic acidosis by greatly increasing the citrate delivery rate in the dialysis solution. In either instance, parallel infusion of calcium gluconate or calcium chloride into the central systemic circulation with careful monitoring of the systemic ionized calcium will prevent inordinant excursions of the systemic ionized calcium level. Such applications are applicable in both the acute intermittent hemodialysis and continuous renal replacement therapy settings.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
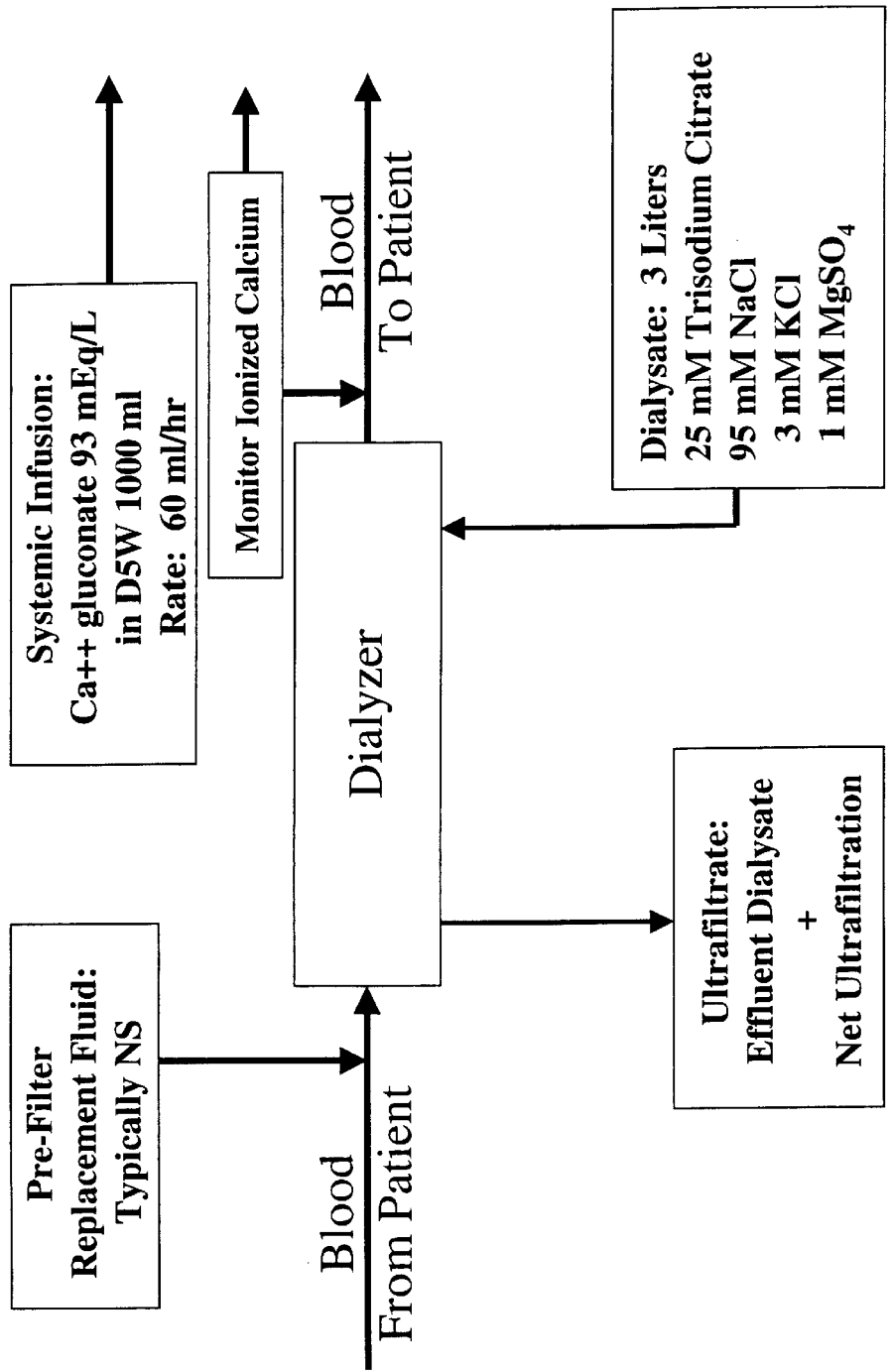
FIG. 1 is a dialysate citrate diagram demonstrating the present invention.

The present invention discloses the use of citrate in dialysate for regional anticoagulation during acute hemodialysis and continuous renal replacement therapy. Instead of intravenous administration, trisodium citrate is a component of the dialysate for dialysis treatment and administered via the dialysis circuit. Inclusion of trisodium citrate into the dialysate fluid of the extra-corporal circuit does not result in direct intravenous infusion. Of note, delivery of citrate via the dialysis circuit, rather than the tradition infusion just before the filter in the external circuit (1–7) allows the separate infusion of a variety of solutions at varying rates into the pre-filter circuit, thus enabling full use of current hemodiafiltration techniques which utilize pre-filter dilution of the delivered patient's blood in the extracorporal circuit. None of the currently practiced methods of citrate regional anticoagulation, utilizing pre-filtrate delivery of TSC (1–7) are readily compatible with hemodialfiltration (CVVHDF).

In one embodiment of the present invention, there is provided a dialysate containing trisodium citrate.

In another embodiment of the present invention, there is provided a method of treating an individual having a renal disease by applying acute hemodialysis to the individual using the dialysate disclosed herein, wherein the dialysate is administered via dialysis circuit. Preferably, the dialysate flows at a rate of from about 300 ml/hr to 1500 ml/hr. In a preferabe aspect, the dialysate has a citrate concentration of 25 mM, and the amount of citrate delivered to the extracorporal circuit is from about 7.5 mmoles/hour to 37.5 mmoles/hour.

In still another embodiment of the present invention, there is provided a method of treating an individual having a renal disease by applying continuous renal replacement therapy to the individual using the dialysate disclosed herein, wherein the dialysate is administered via dialysis circuit. Preferably, the dialysate flows at a rate of from about 300 ml/hr to 1500 ml/hr. Still preferably, the dialysate has a citrate concentration of 25 mM, and the amount of citrate delivered to the extracorporal circuit is from about 7.5 mmoles/hour to 37.5 mmoles/hour.

In yet another embodiment of the present invention, there is provided a method of providing regional anticoagulation during acute hemodialysis in an individual in need of such treatment by administering the dialysate disclosed herein to the individual via dialysis circuits.

In still yet another embodiment of the present invention, there is provided a method of providing regional anticoagulation during continuous renal replacement therapy in an individual in need of such treatment by administering the dialysate disclosed herein to the individual via dialysis circuits.

Additional applications of the dialysate disclosed herein include correction of severe systemic metabolic alkalosis by greatly reducing the citrate delivery rate in the dialysis solution, and correction of severe systemic metabolic acidosis by greatly increasing the citrate delivery rate in the dialysis solution. In either instance, parallel infusion of calcium gluconate or calcium chloride into the central systemic circulation with careful monitoring of the systemic ionized calcium will prevent inordinant excursions of the systemic ionized calcium level. Such applications are applicable in both the acute intermittent hemodialysis and continuous renal replacement therapy settings. Preferably, for correction of severe systemic metabolic alkalosis, the citrate delivery rate is from about 0 mmol/hr to about 15 mmol/hr, whereas for correction of severe systemic metabolic acidosis, the citrate delivery rate is from about 25 mmol/hr to about 37.5 mmol/hr.

The following examples are given for the purpose of illustrating various embodiments of the invention and are not meant to limit the present invention in any fashion.

EXAMPLE 1
Human Subject Protocol

Up to 100 patients are enrolled. All patients with acute renal failure requiring continuous renal replacement therapy (CRRT) are screened for enrollment. Those who have an absolute or relative contraindication to heparin are not randomized, but are offered dialysis-citrate regional anticoagulation. All other eligible patients are then randomized between conventional therapy (systemic heparin and Dianeal dialysate) and a dialysate-citrate group. None of the participants are younger than 18 years of age. An equal number of males and females, Caucasians and Afro-Americans are screened and enrolled. None of the special populations are enrolled at risk.

This is an intention to treat protocol, with randomization occurring immediately following the decision to screen the patient for continuous renal replacement therapy. Patients are followed for as long as they receive continuous renal replacement therapy, and until they reach a defined end point. Each subject is enrolled in only a single arm of the study. Once reaching a pre-defined end-point, the individual subject is not re-randomized. Subsequent continuous renal replacement therapy and choice of anticoagulation will be at the discretion of the Consulting nephrologist responsible for the patient's care.

The randomized, prospective human subject protocol is intended to compare the safety and efficacy of systemic heparin to that of trisodium citrate (TSC) which is included in the dialysate at 25 mM as a regional anti-coagulant of the extra-corporal dialysis circuit. The patients are screened if they have acute or chronic renal failure and are going to be treated with continuous renal replacement therapy; those patients who have an absolute or relative contraindication to heparin therapy will be excluded from the randomized protocol.

EXAMPLE 2
Dialysate Trisodium Citrate as a Regional Anticoagulant

Heparin and citrate are approved for extra-corporal anti-coagulation. Inclusion of trisodium citrate in the dialysate is viewed by the FDA as a device and not a drug. In accord with the package labeling, trisodium citrate is not given directly intravenously (see FIG. 1 for dialysate citrate diagram).

4% Trisodium citrate (TSC) is commercially available from Baxter Fenwall and Tricitrasol triCitrasol (46.7% TSC) is commercially available from Citra Anticoagulants, Inc. (NB: FDA Warning TOO-16 on Apr. 14, 2000 has apparently caused triCitrasol to be recalled). Two approaches are used for the production of citrate-containing dialysate. The preparation of a 3-liter unit of dialysate is described below since this unit would be a convenient volume:

A: 4% TSC from Baxter Fenwall is in dialysate in the following mixture: a 3 liter bag of dialysis solution is made consisting of 2.5 liter of ½ Normal Saline (78 mEq NaCl), 500 ml of 4% TSC and 15 ml 23% NaCl (American Reagents Laboratory) for a final concentration of 23.3 mM citrate, 155 mM sodium and 85 mM chloride. The osmolality is slightly hypotonic at 263 mOSM. Adjustments of the osmolality can be made by further additions of small volumes of 23% NaCl.

B: Tricitrasol is in dialysate in the following mixture: a 3 liter bag of dialysis solution is made consisting of 3 liter of ½ Normal Saline (78 mEq NaCl), 46 ml of 46.7% TSC (TricCitrasol) for a final concentration of 25 mM citrate, 3 mM KCl, 1.5 mM $MgSO_4$, and 10 mM NaCl. This solution is nearly isotonic. Adjustments of the osmolality can be made by further additions of small volumes of 23% NaCl.

The described dialysates are totally free of bicarbonate and calcium. Small amounts of phosphate could also be added if clinically warranted. The dialysis flow rate is usually maintained at 1000 ml/hr; it is expected at this flow rate the dialysate citrate maintains the post-filter ionized calcium level between 0.25 and 0.50 mM. The dialysate flow rate could be varied between 300 and 1500 ml/hr to vary the rate of citrate administration; alternatively, the dialysis flow rate could be maintained at a constant rate and reciprocal changes in the Trisodium citrate and NaCl concentration in the dialysate solution could be made with proper maintenance of isotonicity.

Systemic calcium infusion into a central line (separate from the dialysis access) is used as needed to maintain systemic ionized calcium between 1.0 and 1.2 mM.

EXAMPLE 3
Study Methodology

This is an open-label randomized efficacy trial in patients with requiring dialysis kidney failure. All appropriate patients are enrolled from the inpatient renal consultative service at UAB Hospital. All patients requiring hemodialysis patients are screened for enrollment in the protocol, but there is a concerted attempt to enroll all consecutive patients in the protocol. Trisodium citrate or heparin is administered during the course of continuous renal replacement therapy unless its use is discontinued due to the failure to achieve acceptable anticoagulation or development of serious adverse events.

Patients with an absolute contraindication to heparin use (low platelets, active bleeding, immediate post-operative course) are not randomized at screening and are not included in the intention to treat protocol. At the discretion of the Consulting nephrologists, such patients may be offered dialysate trisodium citrate regional anticoagulation. All other patients requiring continuous renal replacement therapy for at least 72 hours are randomized to one of the following two treatment arms:

a) Standard Therapy with systemic heparin sufficient to increase the partial thromboplastin time to 1.5–2 times control in the extra-corporal circuit, and with Dianeal dialysate.

b) Dialysate trisodium citrate at 25 mM delivered a t 1000 ml/hr to effect regional anticoagulation as judged by the measured ionized calcium at the immediate post-filter sample port.

All continuous renal replacement therapy is performed with the Cobe PRISMA or Baxter BM-11 devices.

EXAMPLE 4
Primary Endpoint (Efficacy)

The duration of total dialysis therapy with each extracorporal circuit before clotting or adverse events precludes the continuation of the treatment with that set up. Patients who require routine replacement of the extra-corporal circuit at 48–72 hours can continue in the same treatment arm of the protocol. If a patient has to be temporarily disconnected from the continuous renal replacement therapy device due to clinical exigencies (radiological procedures, surgical operating room visits, etc.), the external circuit is flushed and placed on by-pass, and therapy resumes when the patient is returned to the Intensive Care Unit. The total elapsed time of therapy refers to hours of actual continuous renal replacement therapy, with 72 hours being the maximal period allowed with an individual extra-corporal set-up.

The effectiveness of the anticoagulation therapy is also judged by comparison of standard urea clearances, obtained by from the flow rates and urea reduction ratios at 36 hours and at 72 hours of therapy in an individual patient.

EXAMPLE 5
Secondary Endpoints (Safety)

Systemic and post-filter ionized calcium are monitored and maintained with in predetermined limits in patients receiving trisodium citrate therapy. Excursions out of these limits constitutes a secondary end point which is recorded for each patient, but does not terminate the therapy.

The effects on acid-base balance, as assessed by periodic arterial blood gas determinations and measurement of the anion gap is determined and recorded on a regular basis for each patient, but does not terminate the protocol unless in the judgment of the Consulting nephrologist an acid-base abnormality has developed which impairs the continuing care of the patient.

The effects on systemic coagulation parameters (prothrombin times and partial thromboplastin times) are regularly determined and recorded for each patient. The development of "citrate toxicity", as manifested by myocardial depression, changed QT interval and/or new-onset arrhythmias during the therapy is recorded for each patient.

The development of critical bleeding episodes during systemic heparin therapy constitutes an end point which terminates the protocol in that individual patient. Any other reason for discontinuing therapy in a given patient, including death, discontinuation of dialysis support, or in the clinical judgment of the Consulting nephrologist is recorded and constitutes an end point for the protocol in that individual patient.

EXAMPLE 6
Inclusion and Exclusion Criteria

Patients of either sex with either oliguric or non-oliguric acute renal failure due to surgery, trauma, crush syndrome, hemodynamic shock, transient hypotension secondary to coronary events, sepsis, drugs or a similar condition are eligible. The decision to provide dialytic support and the chosen modality of therapy for the individual patient is made by the Consulting Nephrologist in consultation with the primary physician of record.

Acute renal failure is defined by a rise in serum creatinine from a baseline value of <1.8 mg/dl (documented or by history) to 3.0 mg/dl following surgery, trauma, an episode of hypotension or the onset of sepsis. A drop in creatinine clearance to less than 25 ml/min in a patient with previously normal kidney function (by history) also defines acute renal failure. Patients with chronic renal failure or End Stage Renal Disease who require dialysis in the Intensive Care Unit setting may also be enrolled in the study. The decision to institute dialysis support and the chosen modality will be made by the Consulting Nephrologist.

The exclusion criteria: (1) patients for whom there is a contraindication against any type of dialysis treatment (intermittent hemodialysis, CAVH, CVVH, CAVHD, CAVHDF, peritoneal dialysis) at the screening evaluation; (2) clear and irreversible disease expected to have a rapidly fatal course; (3) serious ventricular arrhythmias or conduction defects shall exclude the patient from the protocol; (4) known hypersensitivity to citrate; and (5) females of childbearing potential who are pregnant or suspected to be pregnant.

Throughout the duration of the study, all subjects receive the usual standard care for renal failure including optimization of fluid and nutritional status, administration of medications and therapies as needed for the treatment of other ongoing medical problems, discontinuation or minimization of the use of nephrotoxic agents, and adjustment of medication doses as appropriate for the level of renal dysfunction. Parameters assessed include total and ionized serum calcium levels, post-filter ionized calcium in the extra-corporal circuit, creatinine clearance, serum creatinine, BUN, serum Na, K, Cl, and $HCO_3$, arterial blood gases, serum albumin, PT and PTT, CBC with platelets, urine volume, urinary excretion of Na, K, Cl, and protein. Concomitant medications such as furosemide, mannitol, dopamine, and other pressors as well as dialysis therapy are recorded, and maybe continued/instituted at the discretion of the Consulting nephrologist and/or primary physicians caring for the patients. Clinical observations and routine hematology/blood chemistry provide safety and tolerability information.

Once a patient reaches a pre-defined end point, then the study protocol is terminated in that individual patient. The Consulting nephrologist will then be permitted to institute what ever for of continuous renal replacement therapy is in their clinical judgment indicated for the patient. These patients will not be re-entered into the protocol by re-randomization. No interview or questionnaire will be used. The principal investigator or designee will obtain the appropriate signed consent from the patient, or legal representative, and also complete a detailed flow sheet for each patient.

Risks and Precautions

During the screening period, the principal investigator or designee determines whether subjects with renal failure are eligible for enrollment. The determination of the need for dialysis is made by the consulting nephrology attending, and the desirability or necessity of avoiding heparin anticoagulation during continuous renal replacement therapy is made in consultation with the primary attending.

Safety is monitored continuously at the sites by the Consulting Nephrologist, primary attending and critical care nursing staff. Laboratory values, vital signs and clinical adverse events will be evaluated for each patient. All adverse events, whether or not considered related to the use of TSC or heparin, are recorded on the flow sheet. If the adverse event is considered serious or life-threatening, it is reported within 24 hours to the IRB with a written notification to follow within 3 working days.

Patients have the right to withdraw from the study a t any time for any reason. The Consulting Nephrologist and primary care attending also have the right to withdraw patients from the study in the event of inter current illness, adverse events, treatment failure, protocol violations, administrative reasons, or other reasons. Such withdrawals is fully documented for post-hoc review. Normal treatment is not withheld. Continuous renal replacement therapy may be temporarily interrupted for radiological studies, operative room visits, or other therapies.

Discussion

Currently, no other effective alternative anticoagulant is available for use in patients who have an absolute contraindication to systemic heparin therapy. The present invention describes a dialysis solution which contains trisodium citrate that would not be administered intravenously, wherein trisodium citrate serves as a regional anticoagulant. A major advantage of this approach is that it would be compatible with the current continuous renal replacement therapy devices and modalities (including CAVHDF) in clinical use and could be readily adapted to acute intermittent hemodialysis, and even chronic outpatient hemodialysis therapy. Dialysate trisodium citrate provides an effective alternative anticoagulant for patients who have an absolute contraindication to systemic heparin therapy.

Excessive citrate administration can cause metabolic alkalosis and symptom due to depressed systemic ionized calcium levels. These side effects can be avoided by judicious administration of systemic calcium, monitoring of the ionized calcium levels and the acid-base parameters of the patient. These monitors are regularly obtained in all critically ill patients in intensive care units.

The rate of citrate administration in the dialysate which would achieve optimal regional anticoagulation has not been evaluated at this time. It is expected that a dialysate containing 25 mM trisodium citrate delivered at 1000 ml/hr will adequately reduce the post-filter ionized calcium to 0.35–0.5 mM, and will also adequately replace the bicarbonate which would be lost from the patient during dialysis with a bicarbonate-free dialysate. Nevertheless, the rate of citrate administration can be varied by changing the rate of dialysate delivery from 300 ml/hour to 1500 ml/hr, or varying the trisodium citrate concentration in the dialysate solution which would then be delivered at a constant rate of 1000 ml/hour.

The following references were cited herein.
1. Lohr J W, et al., Am J of Nephrology. 1988;8:368–72.
2. Lohr J W, et al., Am J Kidney Dis. 1989;2:106–7.
3. Mehta R L, et al., Kidney Int. 1990;38:976–81.
4. Pinnick R V, et al., N Eng J Med. 1983;308:258–63.
5. Palsson R, et al., Kindey Int. 1999;55:1991–7.
6. Meier-Kriesche H U, et al. Am J of Kidney Dis. 33(4):e8, 1999.
7. Tolwani A, et al. Kidney Int. submitted 2000.
8. Ahmad S, et al., Am. J. Kidney Dis. 35: 493–499, 2000.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of providing regional anticoagulation therapy in an individual receiving acute hemodialysis, comprising the step of:

administering to said individual an effective amount of a trisodium citrate dialysate into the dialysate fluid of the extra-corporal dialysis circuit, wherein said dialysate has a concentration range of citrate of from about 12.5 mM to about 37.5 mM.

2. A method of providing regional anticoagulation therapy in an individual receiving continuous renal replacement therapy, comprising the step of:

administering to said individual an effective amount of a trisodium citrate dialysate into the dialysate fluid of the extra-corporal dialysis circuit, wherein said dialysate has a concentration range of citrate of from about 12.5 mM to about 37.5 mM.

3. The method of claim 1, wherein said dialysate flows at a rate of from about 300 ml/hr to about 1500 ml/hr.

4. The method of claim 3, wherein said dialysate has a citrate concentration of 25 mM and said citrate is delivered to the extracorporal circuit in an amount of about 7.5 mmoles/hour to about 37.5 mmoles/hour.

5. The method of claim 2, wherein said dialysate flows at a rate of from about 300 ml/hr to about 1500 ml/hr.

6. The method of claim 5, wherein said dialysate has a citrate concentration of 25 mM and said citrate is delivered to the extracorporal circuit in an amount of about 7.5 mmoles/hour to about 37.5 mmoles/hour.

* * * * *